United States Patent [19]

Swezey et al.

[11] Patent Number: 5,425,378

[45] Date of Patent: Jun. 20, 1995

[54] ADVANCED POSTURE-MONITORING DEVICE

[76] Inventors: Robert L. Swezey, 10532 Garwood Pl., Los Angeles, Calif. 90024; Richard Swezey, 148 N. Wilton Pl., Los Angeles, Calif. 90004

[21] Appl. No.: 273,595

[22] Filed: Jul. 11, 1994

[51] Int. Cl.⁶ ............................................. A61B 5/103
[52] U.S. Cl. ..................................... 128/782; 128/774
[58] Field of Search ...................... 128/779, 781, 782; 2/171, 171.1

[56] References Cited

U.S. PATENT DOCUMENTS

| | | | |
|---|---|---|---|
| 2,153,146 | 4/1939 | Holmes | 2/171.1 |
| 2,565,381 | 8/1951 | Leighton | 128/782 |
| 4,586,515 | 5/1986 | Berger | 128/782 |
| 4,742,581 | 5/1988 | Rosenthal | 2/171 X |
| 4,777,965 | 10/1988 | Allison et al. | 128/782 X |
| 4,800,897 | 1/1989 | Nilsson | 128/782 |
| 4,928,709 | 5/1990 | Allison et al. | 128/782 |
| 5,158,089 | 10/1992 | Swezey et al. | 128/782 |
| 5,203,346 | 4/1993 | Fuhr et al. | 128/782 X |

*Primary Examiner*—Sam Rimell
*Attorney, Agent, or Firm*—J. E. McTaggart

[57] ABSTRACT

A monitoring unit is mounted atop headgear fitted with a proportional level sensor which detects head inclination in the saggital plane. A battery powered microcontroller, interfaced with the level sensor, monitors the head tilt and provides a sonic indication whenever the tilt exceeds preset limits to the front or rear. The use of a proportional level sensor of the capacitive/fluid type enables the microcontroller to be configured to allow the user to preset different tilt limits, and to select different modes, for example beginning or advanced training, sitting, standing or exercising body positions, and to set up a designated training session duration, timed by sonic indication, during which the number and direction of head tilt deviations detected may be counted. Such statistical data may be displayed to the user on an LCD display. With the level sensor mounted directly to one side of the headgear, the monitor unit in a housing atop the headgear may specially non-rigidly attached to provide a degree of wobble or totter perceptible to the user as kinesthetic/proprioceptive feedback, in addition to the audible biological feedback received from the sonic tilt limit indication. The microcontroller system may be specially configured to recognize and ignore gross movements such as reaching or bending, while still feeding back to the user the finer postural deviations.

18 Claims, 4 Drawing Sheets

ADVANCED POSTURE-MONITORING DEVICE

This application is related to U.S. patent application 07/924,718 by the same inventors, filed on Aug. 4, 1992, now abandoned, which was a continuation-in-part of U.S. patent application 07/726,256 by the same inventors, filed on Jul. 5, 1991 and issued as U.S. Pat. No. 5,158,089 on Oct. 27, 1992.

FIELD OF THE INVENTION

The present invention relates to fitness-training apparatus and more particularly it relates to advancements in a headband posture monitoring equipment directed to sensing head tilt in the saggital plane and providing bio-feedback to the wearer for purposes of evaluating and improving posture especially as related to the head, neck, shoulders and spine in a standing, sitting or exercising position.

BACKGROUND OF THE INVENTION

It has been established that, given symmetry of the body about the saggital plane (the median vertical plane dividing the body into right and left halves), a key element of posture is the inclination of the head in this plane statically and dynamically with body movement, along with the necessary linear elongation of the neck and spine required for truly good posture. There is an optimal range of head inclination within which the weight of the head tends to be balanced and thus minimize the amount of force required from the supporting muscles, ligaments and bones. Generally, individuals whose normal head positioning is held within this optimal range tend to enjoy physical wellbeing and good appearance. Outside of this optimal range, unbalancing of the weight of the head upsets the muscle and ligament equilibrium, and, if continued over a length of time, generally leads to symptoms of muscle and ligament strain and potential discomfort or disfunction along with the resultant detriment to the appearance and self-esteem.

For those who seek to overcome harmful posture behavior patterns, a posture training program will benefit from biofeedback and assertive technical reinforcement to accelerate the process and ensure more lasting postural improvement. Conventional practice often relies heavily on the verbal admonishments of others including professionals and may require an extraordinary level of self-discipline and self-awareness, more than is reasonable to expect in many individuals.

Research leading to the present invention has found therapeutic benefit in posture training which utilizes a headgear device to monitor inclination of the head in the saggital plane as indicative of posture of the upper body, including the head, neck and shoulders, and to assertively remind the individual through bio-feedback whenever this posture lapses to an incorrect condition. Furthermore, the effectiveness of such training may be enhanced by optimizing the amount, distribution and dynamics of weight of the device as perceived by the user. The effect of the corrective action extends beyond the actual duration of each training session by creating within an individual a "muscle-kinesthetic memory" so that even when the device is not in use or activated, the individual actually "recalls" and retains proper head position to the benefit of related neck and back posture.

PRIOR ART

Posture training devices for attachment to the body have been proposed as exemplified by U.S. Pat. Nos. 4,958,145 to Morris, 4,055,168 to Miller et al, 4,007,733 to Celeste et al, 3,582,935 to Verhaeghe, 3,608,541 to Hall and 4,871,998 to Chailloua; all of these utilize some form of harness or belt for attaching sensing apparatus to the trunk of the body around the waist or shoulders.

U.S. Pat. No. 4,493,328 to Saito discloses a light sensing structure attached to the chest and shoulders operating in conjunction with a head-mounted light source for treating spasmodic torticollis. U.S. Pat. No. 4,869,509 to Lee discloses a GOLFER'S HEAD MOVEMENT INDICATOR as a golfer's training aid which, mounted inside a golfer's cap, audibly signals an improper head motion during a golf swing. The Lee patent further references a number of other patents addressing golfing posture.

The abovementioned and other known art of posture monitoring and training devices have failed to specifically and satisfactorily apply bio-feedback principles and techniques to the correction of standing, sitting and exercising posture of individuals afflicted with posture problems.

OBJECTS OF THE INVENTION

It is a primary object of the present invention to provide a headgear-mounted posture-monitoring device for sensing the tilt of a wearer's head in the saggital plane and providing indication to the wearer whenever the tilt reaches predetermined deviation limits to the front and rear, so as to enable the perception and maintenance of proper posture.

It is a further object to provide the device with user capability of setting or selecting different limits at which tilt will be indicated.

It is a further object to provide capability of registering and indicating additional data relating to posture monitoring and training performed with the device, such as the number of front and rear tilt deviations detected.

A still further object is to configure the monitor unit in such a manner that, in addition to audible feedback, the wearer will receive kinesthetic biofeedback, due to the wobble or totter of the unit, so as to further contribute to maximizing proper spinal elongation.

SUMMARY OF THE INVENTION

The abovementioned objects have been realized in the present invention of a posture-monitoring device including a level sensor and a monitor unit mounted to headgear, which may include a visor, via a central strap of fabric or other material positioned along the saggital plane and secured by a similar transverse strap. The battery-powered monitor unit includes a sonic indicator which becomes actuated in response to sensed head tilt deviations which exceed the preset limits.

Options for implementing the level sensor include a simple level-sensing switch such as conductive fluid or weighted pendulum type; however, in a preferred embodiment, a fluid-capacitive proportional tilt sensor is interfaced to a microcontroller which is readily made to provide selection of the front and rear tilt limits. The microcontroller may be made to provide additional capabilities such as a timing of training sessions and recording of the number and direction of tilt deviations detected, and may be made to disregard certain extraneous gross head movements.

DESCRIPTION OF THE DRAWINGS

The above and further objects, features and advantages of the present invention will be more fully understood from the following description taken with the accompanying drawings in which.

DETAILED DESCRIPTION

Figure 1:
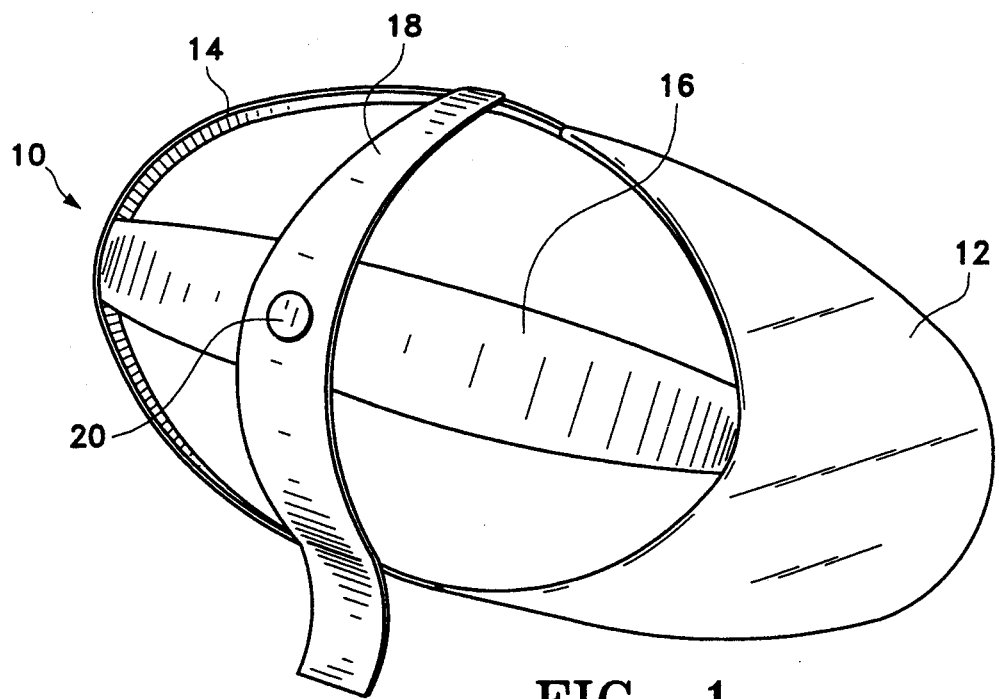
FIG. 1 is a perspective top view of a visor-headband embodiment of a posture-monitoring device in accordance with the present invention.

In the perspective top view of FIG. 1, headgear 10 for carrying a posture-monitoring device of the present invention has a sun visor brim 12 attached to a headband 14 which has a central strap 16, formed to follow the outline of the head along the wearer's saggital plane. Strap 16 is attached to headband 14 at front and rear, and a cross strap 18 is adjustably attached to headband 14 at two opposite side locations immediately above the ear. Strap 16 is made adjustable in length at the rear of the headband 14. At the intersections of straps 16 and 18, a fastener 20 is provided for attaching a monitor unit (not shown). Adjustments for head size and shape are provided by conventional adjustable fastening means such as dome or slide type fastenings: the headband 14 and straps 16 are made adjustable at the rear, and cross strap 18 is made adjustable in length and lockable on both sides. Preferably visor peak 12 is made removable from headband 14, e.g. by means of snap fasteners.

Figure 2:
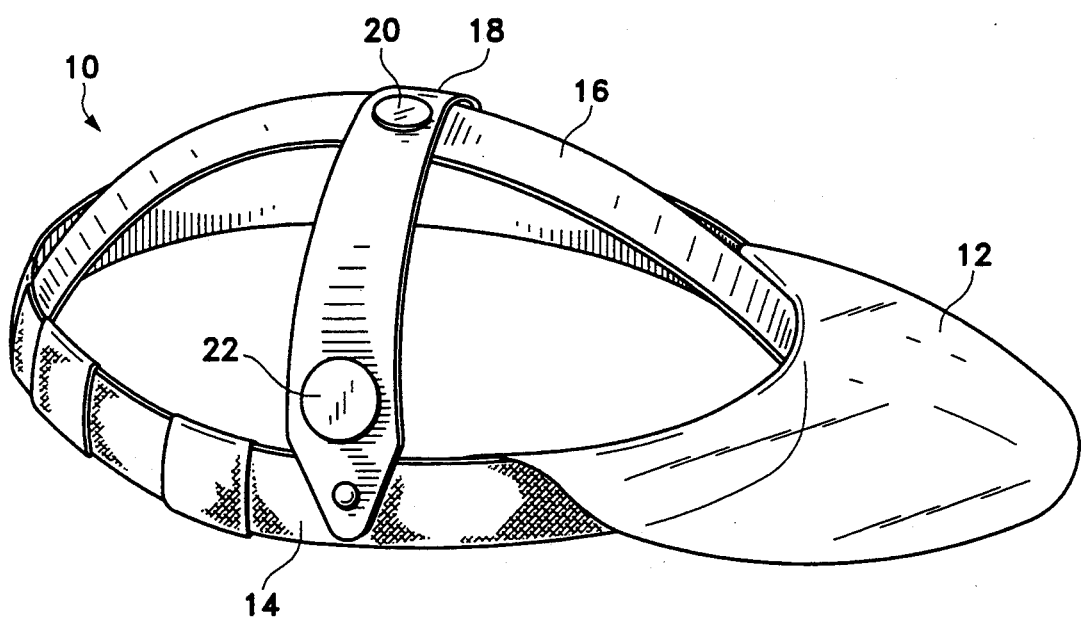
FIG. 2 is a perspective view of the visor-headband of FIG. 1.

FIG. 2 is a perspective view of the headgear unit 10 of FIG. 1, showing visor peak 12, headband 14, straps 16 and 18, and monitor fastener 20. A level sensor element 22 is shown attached on one side of strap 18.

Figure 3:
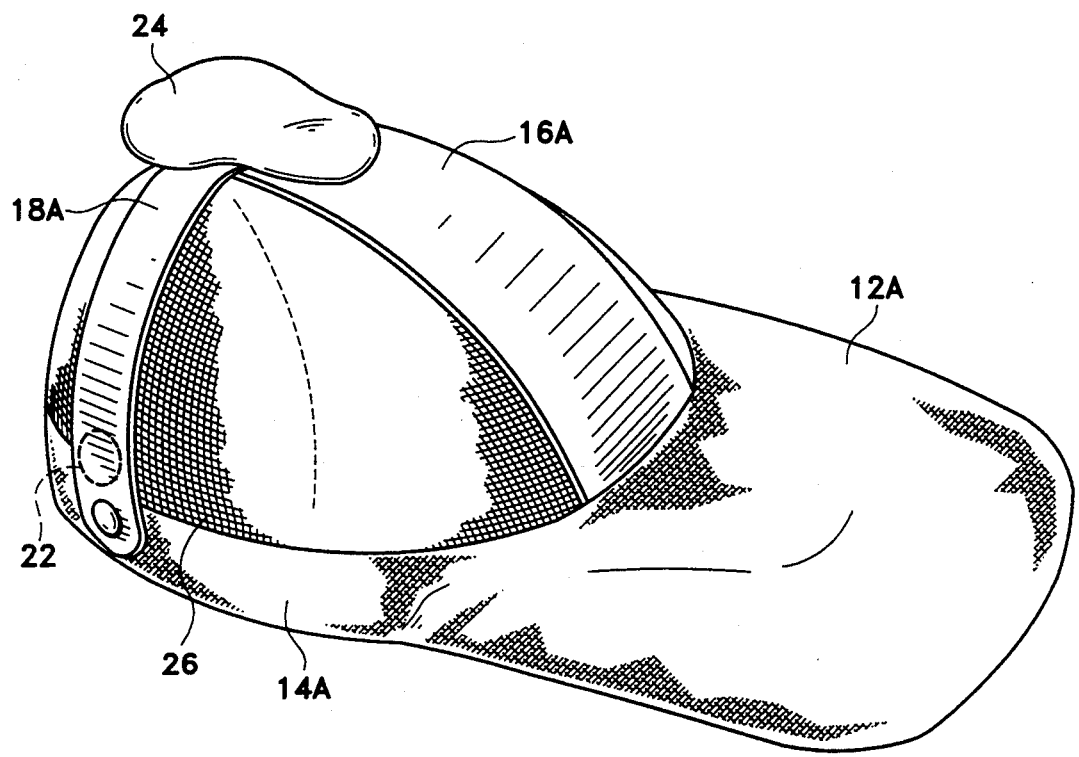
FIG. 3 is a perspective view of a lined hat embodiment of the posture-monitoring device of the present invention.

FIG. 3 is a perspective view of an embodiment of the posture monitor of the present invention wherein the headgear is styled to have a visor peak portion 12A made integral with a headband 14A. A monitor unit 24, shown attached at the intersection of straps 16A and 18A, includes a sonic indicator, battery, controls and circuitry to work in cooperation with level sensor 22, which may be mounted within one side of strap 18A as shown, in either an exposed or concealed manner. A lightweight underhat lining 26, seen between straps 16A and 18A, is made from breathable terrycloth-like material; as well as being absorbent of perspiration, lining 26 serves to in effect grip the user's hair and to distribute the weight of the monitor unit 24 so as to avoid any distracting pressure points and to allow the weight of the monitor unit to be fully perceived by the user.

Figure 4:
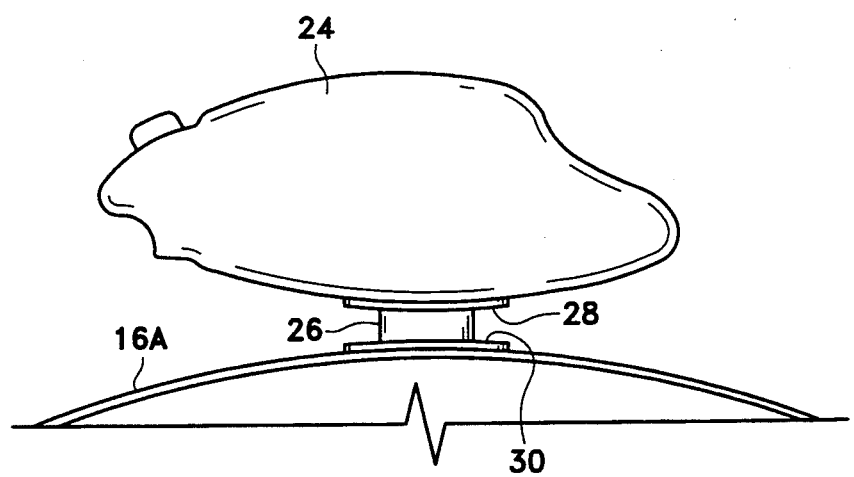
FIG. 4 is an enlarged side view of a portion of the posture-monitoring device of FIG. 3.

FIG. 4 is an enlarged side view of the monitor unit 24 showing it mounted onto the uppermost crown portion of strap 16A by a mounting pedestal 26 which is preferably attached to unit 24 by a first mounting plate 28 and to strap 16A by a second mounting plate 30 fitted with a detachable fastener. The necessary electrical connections to unit 24 from the level sensor may be provided with a detachable connector. The mounting of unit 24 via pedestal 26 is preferably made resilient and pivoted, for example by means of a ball bearing or fulcrum pivot which may be surrounded by a sleeve of resilient material such as plastic foam. This flexible pivoted mounting working in cooperation with the mass of monitor unit 24 introduces a controlled amount of wobble or totter for to provide a kinesthetic/proprioceptive effect perceived by the user for spinal elongation. This effect may be further enhanced by fitting unit 24 with a pocket of weighted viscous material or fluid.

The mounting 26 and weight of unit 24 are made such that the wearer will perceive it as the principal object on the head, i.e. not over-ridden by the headgear portion.

Figure 5A:
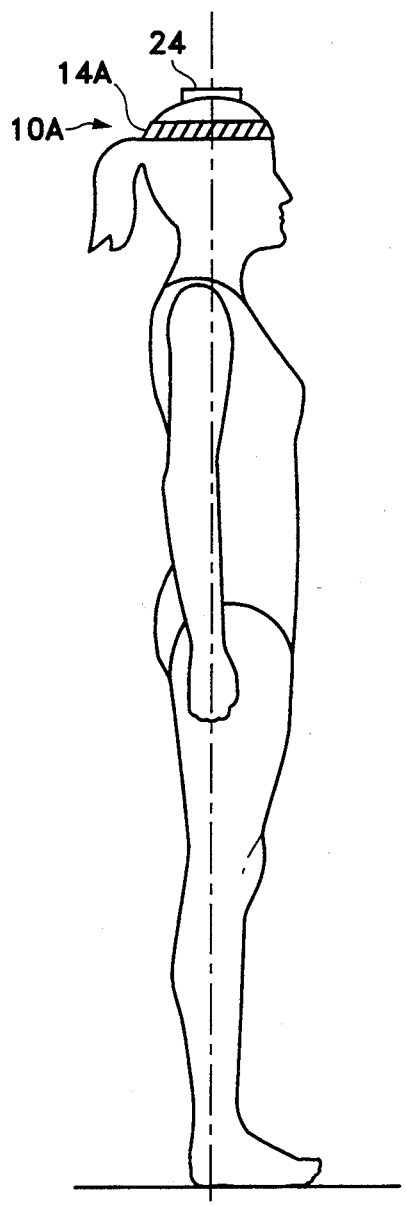
FIG. 5A is a profile of a user wearing a headband posture-monitoring device according to the present invention, illustrating correct standing posture.

FIG. 5A shows a profile of a user wearing a posture-monitoring unit 10A of this invention, illustrating correct posture in a standing position: the vertical line indicates generally linear alignment of the spine, neck and head in balanced relationship. In this style, the headband 14A is worn without a visor peak, in an approximately horizontal position appropriate to the user's hair styling. After an initial setup calibration at a reference neutral-tilt level corresponding to correct posture as shown in FIG. 5A, sensor 22 proportionally measures the tilt angle of the head in the body's saggital plane relative to the reference-level. The tilt angle is continuously monitored by unit 24, and generates an audible signal whenever the tilt exceeds a preset limit.

Figure 5B:
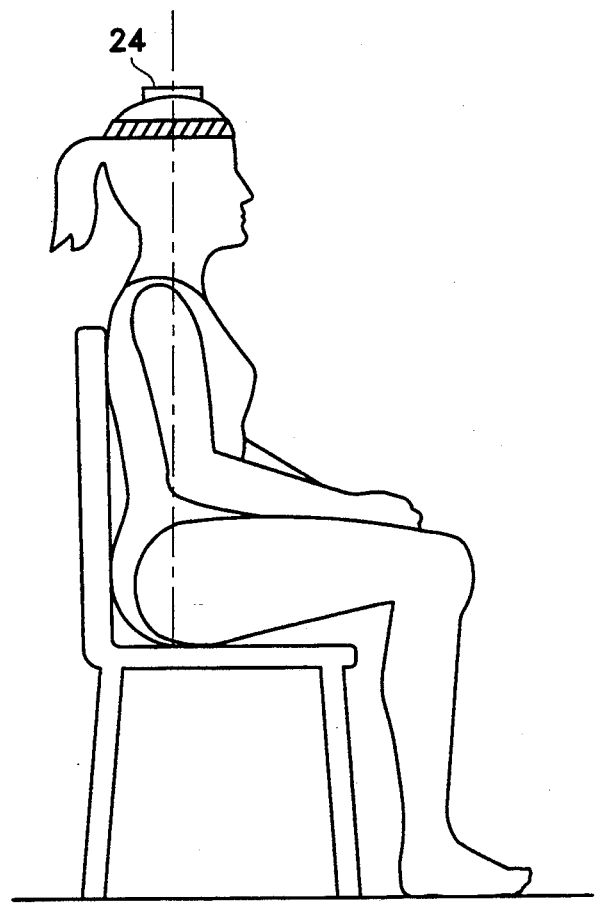
FIG. 5B is a profile of the user of FIG. 5A illustrating correct sitting posture.

In FIG. 5B the user is profiled in a sitting position, again illustrating correct posture with linear spine, neck and head alignment.

Figure 5C:
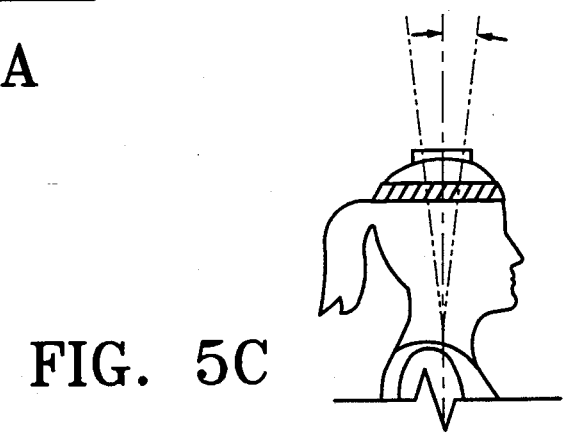
FIG. 5C is a profile of the head of the user of FIGS. 5A and 5B, indicating critical angles of head inclination.

FIG. 5C, shows a profile of the head of the user shown in FIGS. 5A and 5B. Critical angles of head inclination are indicated by phantom lines each side of the vertical line as the head is inclined frontward and backward in the saggital axis about a pivot point located in the neck region. Head inclination within the critical angles is considered indicative of acceptably normal posture, while inclination beyond the critical angles indicates defective posture and need for corrective action. Studies indicate the critical angles fall within a range between 2 and 7 degrees. A value of 4 degrees in both the plus and minus directions has been found to be generally valid and could be built into a simplified version as a fixed value; however, since this value may vary, for example between beginning and advanced training sessions, it is desirable to provide user adjustment for setting the plus and minus tilt levels at which sonic indication is actuated.

It should be noted that in FIGS. 5A-5C, the critical vertical axis corresponding to correct posture, as indicated by the phantom vertical line in each case, passes through several critical body points including the top of the head, the external auditory meatus (ear opening), neck pivot point, shoulder and principal lower support region (seat or foot). It is considered preferable to locate the level sensor 22 of the present invention on this axis, immediately above the ear as shown.

Figure 6A:
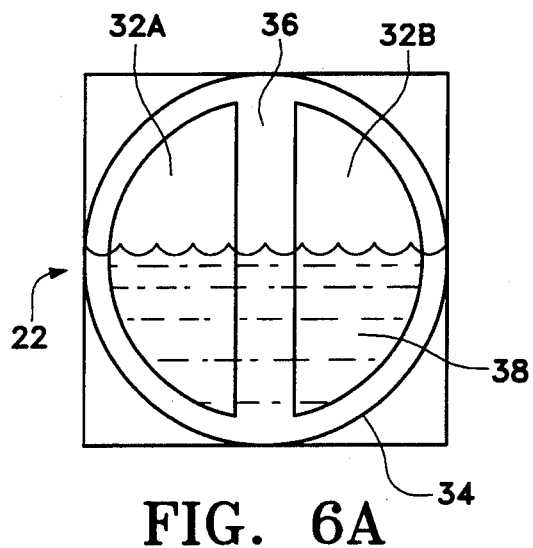
FIG. 6A is representation of a fluid/capacitive type tilt sensor, in a level orientation.

FIG. 6A represents a level sensor 22 (FIGS. 2,3) made in the form of a fluid/capacitive device for measuring the direction of the pull of gravity relative to the sensor, similar to the function of a bubble level. Two capacitors are formed by a pair of metal plates 32A and 32B disposed side by side on one side of a thin chamber 34 opposite a common plate 36 disposed on the opposite side, such that the chamber forms the dielectric for the two capacitors. The chamber is half filled with a non-conductive fluid 38 having a dielectric constant much greater than 1 (that of air). In the neutral, i.e. non-tilted orientation shown in FIG. 7A, it is clear that due to the balanced geometry the two capacitors will have equal capacitance.

Figure 6B:
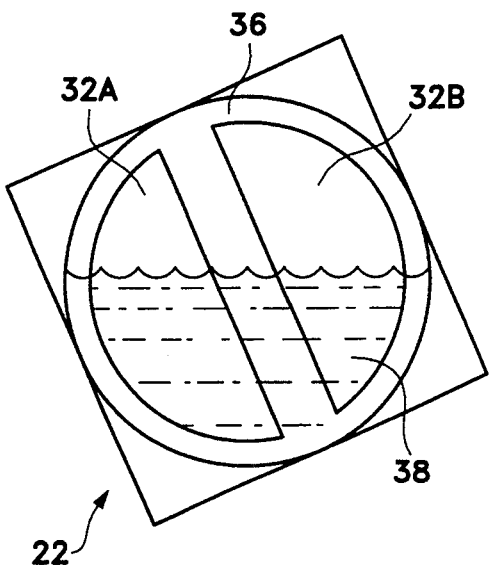
FIG. 6B is representation of the tilt sensor of FIG. 6A in a tilted orientation.

FIG. 6B shows the level sensor 22 tilted at an angle counterclockwise from its neutral orientation in FIG. 6A. Now the area of high dielectric due to fluid 38 between plate 32A and common plate 36 has increased and thus the corresponding capacitance has increased, while the area between plate 32B and the common plate 36 and that corresponding capacitance have decreased. These opposite capacitance changes are proportional to the angle of tilt, and the two capacitance values may be converted to a signal which accurately and continuously represents the angle of tilt.

Figure 7:
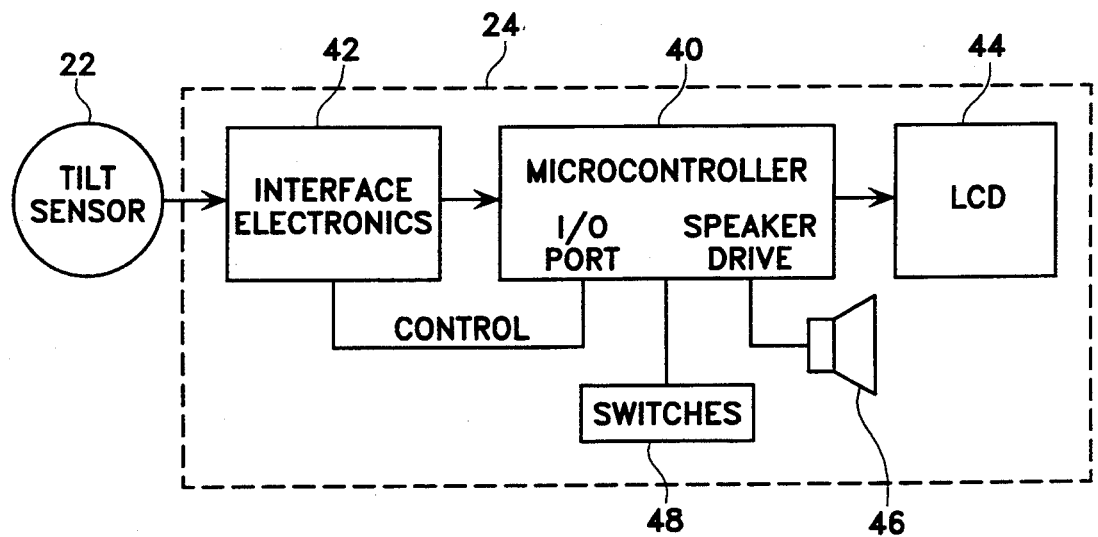
FIG. 7 is a block diagram of a preferred embodiment of the present invention with a microcontroller-based monitor unit operating from the tilt sensor of FIG. 6A-B.

FIG. 7 is a functional block diagram of the circuitry of an embodiment of the device of the present invention in which the monitor unit 24 receives input from tilt sensor 22, which is mounted directly to the headgear rather than to the monitor unit 24 so as to properly measure head tilt independent of the influence of the wobble or totter of the monitor unit 24 previously described.

Within monitor unit 24, a microcontroller 40 cooperates with interface electronics 42 which, connected to the two capacitors in sensor 22, converts the capacitance values into a signal usable by microcontroller 40.

In interface electronics 42, a pair of op-amp oscillators, which may be turned on or off under software control from microcontroller 40, are each tuned in frequency by one of the capacitors in sensor 22.

Microcontroller 40 is a specialized low power unit that includes RAM, ROM, I/O ports, a digital counter, an interval timer and an LCD driver. The program software in the ROM contains the user interface routines and the routines for converting the output of the interface electronics into a value representing the tilt of the sensor. The RAM contains the operating parameters selected by the user by switch group 48 and the processed information from sensor 22. The LCD display driver allows the microcontroller 40 to display the processed information to the user on LCD display 44.

The conversion routine for measuring the tilt angle uses a digital counter in the microcontroller 40 to count the oscillation cycles from each oscillator, and an interval timer to determine the period in which the cycles are counted. The conversion routine first resets the counter to zero. The routine starts the interval timer and enables one of the oscillators to begin oscillating. The counter counts the cycles of oscillation until the interval timer expires. The routine then turns off the oscillator and reads the digital count from the counter. This count is then processed mathematically to determine the capacitance and hence the angle of the tilt sensor 22.

The capacitance values from both capacitors in sensor 22 are read to provide the differential change in the two capacitors so as to enable the mathematical processing to suppress undesired common mode effects such as thermal drift and battery voltage variation. Microcontroller 40 converts and processes the tilt reading several times each second. The tilt readings may be further processed to reduce the effects of jostling of the sensor as the user walks and moves about.

The software contained in the ROM may include routines to further customize the function of the device to the individual user.

Using the keyboard switch group 48 the user may select the tilt angle at which the audio transducer 46 will sound. The user may also select a time duration for which the device will record data and process statistics relating to head position and posture, and transducer 46 may be made to signify the end of a training session of designated duration. The number of possible functions is limited only by the available ROM capacity of the selected microcontroller.

The microcontroller 40 is designed for low power operation. Most of the battery power is consumed by the audio transducer 46 and the interface electronics 42. However, this power consumption is small enough that the device may operate for a sufficiently long time using button cell batteries.

The detailed configuration and programming of microcontroller 40 and interface electronics 42 to accomplish specified objectives are within the knowledge and competence of those skilled in the control electronics and data processing arts.

A typical configuration of the user control switch group 48 could include a mode switch having four positions, e.g. BEGINNING, SEATED, ADVANCED and EXERCISING, and could be made to set a corresponding tilt limit and time duration for each, e.g. 4 degrees/5 minutes or 7 degrees/20 minutes.

Regarding the weight of the monitor housing 24 including it contents, a range from 2.5 to 4 ounces has been found optimal with regard to user perception and comfort.

As an alternative to locating the control switch group 48 and the LCD display 44 in the monitor housing 24, these could be made part of a cable-connected user control panel external to the main headgear unit. Display 44 could be mounted on a narrow support extending from the headgear in the manner of a bicyclist's rear view mirror.

The above referenced U.S. Pat. No. 5,158,089 by the present inventor, discloses still other aspects related to the present invention, particularly addressing relatively simple implementations utilizing discrete step level switches rather than a proportional level sensor and microcontroller.

The invention may be embodied and practiced in other specific forms without departing from the spirit and essential characteristics thereof. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed is:

1. A posture-monitoring device comprising:
a headpiece, worn on a user's head;

weighting means of predetermined weight attached to said headpiece and located substantially in an upper central region thereof for providing the user with a sensation of biological feedback;

proportional tilt-detecting means attached to said headpiece and enabled for acquiring and registering data selected and entered by a person regarding limit values of tilt and for quantitatively measuring angles of frontward and backward tilting of said headpiece in the user's saggital plane relative to a designated reference orientation of the headpiece, thereby detecting instances of such tilting which exceed the limit values of tilt; and a sonic indicator, operationally connected to said tilt-detecting means, enabled to provide the user with sonic indication of the detected instances of excessive tilting.

2. The posture-monitoring device as defined in claim 1 wherein said tilt-detecting means comprises:

a level sensor attached to said headpiece and enabled to sense the angular orientation of said headpiece in the saggital plane relative to a vertical gravitational force reference, and to provide corresponding proportional angular direction information;

interface means operationally connected to said level sensor and enabled to convert angular direction information received from the level sensor into a real time tilt signal containing proportional data representing angle of tilt of the headpiece;

microcontroller means, operationally connected to said interface means and to said sonic indicator; and user input means, operationally connected to said microcontroller means, enabling the user to select a tilt limit;

said microcontroller means being enabled to compare said proportional angular data in the real time tilt signal with the tilt limit and to actuate said sonic indicator whenever the tilt signal is found to exceed the selected tilt limit.

3. The posture-monitoring device as defined in claim 2 wherein the tilt limit is selectable by the user in a working range which includes positive and negative values from 2 degrees to 7 degrees of tilt.

4. The posture-monitoring device as defined in claim 1 wherein said sonic indicator comprises a sonic transducer actuated from an audio tone signal.

5. The posture-monitoring device as defined in claim 4 further comprising a housing containing said interface means, said microcontroller means, said sonic transducer and a power supply battery, said housing being attached atop said headpiece so as to be disposed at a highest point of the user's head and thus constitute at least a portion of said weighting means.

6. The posture-monitoring device as defined in claim 5 wherein said housing is attached resiliently and pivotedly to said headpiece so as to cause a predetermined degree of totter perceptible to the user as kinesthetic/proprioceptive biological feedback.

7. The posture-monitoring device as defined in claim 6 wherein said housing and contents thereof are made to have a total weight within a range from 2.5 to 4 ounces.

8. The posture-monitoring device as defined in claim 4 further comprising a pocket of weighted viscous material affixed to said headpiece so as to cause a predetermined degree of totter perceptible to the user as kinesthetic/proprioceptive biological feedback.

9. The posture-monitoring device as defined in claim 2 wherein said level sensor is attached to said headpiece at a location midway along a lower side portion thereof, so as to locate the level sensor near an axis of saggital plane tilt of said headpiece due to nodding and thus substantially isolate said sensor from effects of displacement of upper regions of said headpiece due to nodding, while enabling the level sensor to measure angles of tilt of the headpiece about the axis of tilt.

10. The posture-monitoring device as defined in claim 5 wherein said headpiece comprises;

a headband surrounding the user's head;

a strap extending from front to back of the headband over the user's head;

attachment means for attaching said housing atop said strap at a highest point of the user's head.

11. The posture-monitoring device as defined in claim 10 further comprising a visor peak extending forward from said headband.

12. The posture-monitoring device as defined in claim 11 wherein said visor peak portion is removably attached to said headband.

13. The posture-monitoring device as defined in claim 10 further comprising a cross strap extending over the user's head between two opposite ear regions of the user.

14. The posture-monitoring device as defined in claim 13 further comprising a lightweight underhat lining made from breathable terrycloth-like material, serving to in effect grip the user's hair and to distribute weight of the monitor unit so as to avoid any distracting pressure points and to create an optimal buffer between the user and said device.

15. The posture-monitoring device as defined in claim 14 further comprising a visor brim attached to said headband and extending forward therefrom.

16. The posture-monitoring device as defined in claim 2 wherein said tilt-detecting means are further enabled to acquire and register user-entered data relating to a time duration of a training session utilizing said device and to accordingly time the training session and cause said sonic indicator to signify an end of the thusly timed training session duration.

17. The posture-monitoring device as defined in claim 16 wherein said tilt-detecting means further comprises a readout display device enabled to display to the user numeric values of operational parameters of said posture-monitoring device such as the user-selected tilt angle and timed training session duration.

18. The posture-monitoring device as defined in claim 2 wherein said microcontroller means and said user input means are configured to enable the user to select from at least two modes of operation each having corresponding preset values of plus and minus tilt limit and timed training session duration.

* * * * *